(12) United States Patent
Tutu

(10) Patent No.: US 7,866,201 B1
(45) Date of Patent: Jan. 11, 2011

(54) ON-LINE FAST RESPONSE DEVICE AND METHOD FOR MEASURING DISSOLVED GAS IN A FLUID

(75) Inventor: Narinder Kumar Tutu, Manorville, NY (US)

(73) Assignee: The United States of America as represented by the United States Department of Energy, Washington, DC (US)

( * ) Notice: Subject to any disclaimer, the term of this patent is extended or adjusted under 35 U.S.C. 154(b) by 573 days.

(21) Appl. No.: 11/697,862

(22) Filed: Apr. 9, 2007

(51) Int. Cl.
*G01N 7/00* (2006.01)
*G01N 33/18* (2006.01)
*G01N 33/26* (2006.01)
*G01N 33/22* (2006.01)

(52) U.S. Cl. ............... 73/19.05; 73/19.07; 73/19.1; 73/861.61

(58) Field of Classification Search ............ 73/19.05, 73/19.06, 19.07, 19.1, 861.52, 861.61
See application file for complete search history.

(56) References Cited

U.S. PATENT DOCUMENTS

| | | | | |
|---|---|---|---|---|
| 3,738,154 A | * | 6/1973 | Henry | 73/19.07 |
| 4,184,359 A | * | 1/1980 | Gracey | 73/19.01 |
| 4,662,219 A | * | 5/1987 | Nguyen | 73/195 |
| 4,750,370 A | * | 6/1988 | Ossyra | 73/861.61 |
| 6,935,189 B2 | * | 8/2005 | Richards | 73/861.04 |
| 2004/0199341 A1 | * | 10/2004 | Gysling et al. | 702/50 |
| 2005/0043900 A1 | * | 2/2005 | Franda et al. | 702/25 |
| 2005/0109078 A1 | * | 5/2005 | Chen et al. | 73/23.29 |
| 2006/0048583 A1 | * | 3/2006 | Gysling | 73/861.04 |

OTHER PUBLICATIONS

"Square-edged orifice." Academic Press Dictionary of Science and Technology. Oxford: Elsevier Science & Technology, 1992. Credo Reference. Jul. 31, 2009.*

* cited by examiner

*Primary Examiner*—Lisa M Caputo
*Assistant Examiner*—Punam Roy
(74) *Attorney, Agent, or Firm*—Mark C. Lang; Michael J. Dobbs; John T. Lucas

(57) ABSTRACT

A method and device for the measurement of dissolved gas within a fluid. The fluid, substantially a liquid, is pumped into a pipe. The flow of the fluid is temporally restricted, creating one or more low pressure regions. A measurement indicative of trapped air is taken before and after the restriction. The amount of dissolved air is calculated from the difference between the first and second measurements. Preferably measurements indicative of trapped air is obtained from one or more pressure transducers, capacitance transducers, or combinations thereof. In the alternative, other methods such as those utilizing x-rays or gamma rays may also be used to detect trapped air. Preferably, the fluid is a hydraulic fluid, whereby dissolved air in the fluid is detected.

11 Claims, 4 Drawing Sheets

ON-LINE FAST RESPONSE DEVICE AND METHOD FOR MEASURING DISSOLVED GAS IN A FLUID

GOVERNMENT INTERESTS

The United States Government has rights in this invention pursuant to Contract No. DE-AC02-98CH10886, between the U.S. Department of Energy (DOE) and Brookhaven Science Associates (BSA).

FIELD OF THE INVENTION

The present invention relates to a device and method for measuring dissolved gas in a fluid, whereby the fluid is substantially a liquid.

BACKGROUND OF THE INVENTION

Unless carefully removed and protected, dissolved gas will generally accumulate in a fluid. Once a gas is dissolved in a fluid the dissolved gas can have various undesirable effects. For example in hydraulic systems, dissolved gas in the hydraulic fluid can cause reduced control stiffness. Dissolved gas may also damage equipment, or pose as a serious safety concern in hydraulic systems as well as other systems. Dissolved gas can cause cavitations, which severely damage system components, as well as cause localized degradation. Dissolved gas can aid corrosion damaging equipment, for example by providing oxygen to the bare metal of a pipe, pump or valve. Inadvertently dissolved gases may pose as a danger to equipment, the environment, or people. For example, Carbon-Monoxide dissolved in a liquid methane fuel cell system may poison a subsequent fuel cell.

Unfortunately, dissolved gas in a fluid is difficult to detect. Current systems employ a cylinder to compress and decompress the fluid, freeing the dissolved air and generating trapped air. The generated trapped air is subsequently detected by various techniques. Unfortunately, this method is slow since each sample must be tediously compressed and decompressed by the cylinder. Furthermore, this method cannot be used in-situ, since the fluid flow through the cylinder must be blocked during compression/decompression of the cylinder. The cylinder may alternately be connected in parallel to a fluid flow, however only a small representative sample can be processed at a time, limiting the accuracy of the detection of dissolved gases in heterogeneous fluids.

Therefore, there is a need for the real-time detection of dissolved gas in a fluid that can be implemented in-situ without requiring the extraction of sample fluids. It is desired to have a system whereby a sensor can be implemented in-line with the flow of the fluid in a manner that allows continuous readings of the dissolved air in the fluid as it passes through the system.

SUMMARY OF THE INVENTION

A method and device for the measurement of dissolved gas within a fluid. A fluid is pumped into a pipe. A measurement indicative of trapped air in the fluid is taken. The flow of the fluid in the pipe is temporarily restricted, creating one or more low pressure regions within the pipe. The one or more low pressure regions induce dissolved air to release out of the fluid as trapped air. A second measurement indicative of trapped air within the fluid after the restriction and within the pipe is taken. Finally, the amount of dissolved air is calculated from the difference between the first and second measurements.

Therefore, it is an object of an embodiment of the present invention for the real-time measurement of dissolved gas within a fluid.

Furthermore, it is an object of an embodiment of the present invention for the real-time, in-situ measurement of dissolved gas within a fluid.

Even still, it is an another object of an embodiment of the present invention for the real-time, in-line measurement of dissolved gas within a fluid whereby the dissolved air in a fluid flow in a system is measured without restricting the flow of the fluid.

It is yet another object of an embodiment of the present invention for the measurement of dissolved air at rates greater than about one reading per second.

It is yet another object of an embodiment of the present invention for the detection of dissolved air in a hydraulic fluid.

It is another object of the present invention for the low cost detection of dissolved gas in a fluid.

It is even yet another object of an embodiment of the present invention for the detection of a dissolved gas from high temperature fluids having temperatures in excess of 500° F.

Even still, it is another object of an embodiment of the present invention for the in-situ detection of dissolved air in a hydraulic fluid.

DETAILED DESCRIPTION OF THE INVENTION

A method and device for the measurement of dissolved gas within a fluid. A fluid is pumped into a pipe. A measurement indicative of trapped air in the fluid is taken. The flow of the fluid in the pipe is temporarily restricted, creating one or more low pressure regions within the pipe. The one or more low pressure regions induces dissolved air to release out of the fluid as trapped air. A second measurement indicative of trapped air within the fluid after the restriction and within the pipe is taken. Finally, the amount of dissolved air is calculated from the difference between the first and second measurements.

Measurements indicative of trapped air may be obtained using various methods as known in the art. Preferably measurements indicative of trapped air are obtained from one or more pressure transducers, capacitance transducers, or combinations thereof. The trapped air measurement is deduced from known pressure, pressure drop or capacitance probe measurement techniques. Pressure drop includes both mean and turbulent fluctuating components, as known in the art. For example, for the case in which the pressure drop is dominated by the hydrostatic head (assuming the sensor is oriented in the vertical direction), the void fraction, volume fraction of gas in a gas-liquid system, of air is directly related to the pressure drop. In the alternative, other methods such as those utilizing x-rays or gamma rays may also be used to detect trapped air. Preferably, the fluid is a hydraulic fluid, whereby dissolved air in the fluid is detected.

Figure 1:
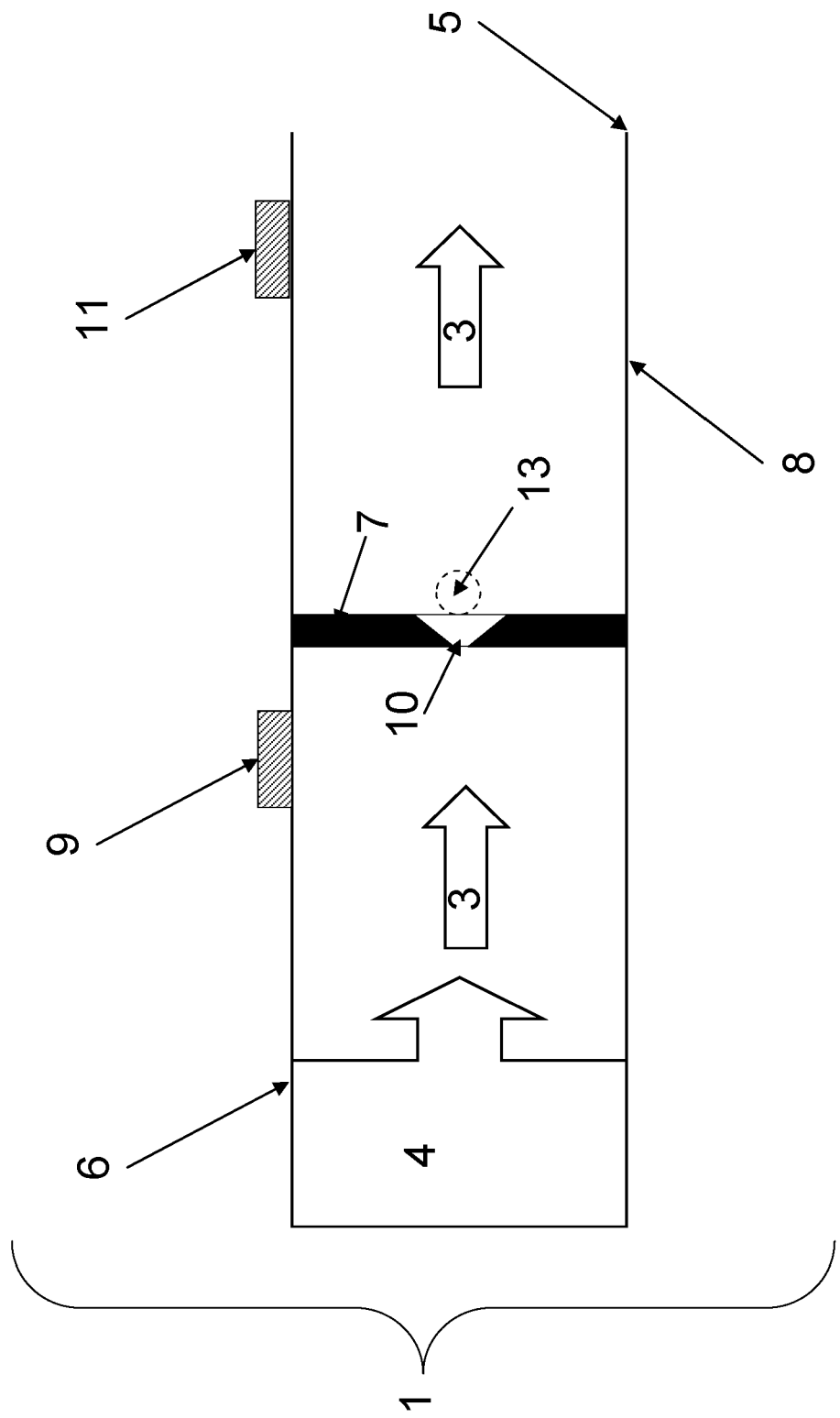
FIG. 1 is the preferred embodiment of the present invention utilizing an orifice plate to restrict the flow of the fluid.

The preferred embodiment 1 shown in FIG. 1, has a pump 4, a pipe 5 a first set of one or more sensors 9, an orifice plate 7, and a second set of one or more sensors 11. The pipe 5 has a first end 6 and a second end 8. The pump 4 is adjacent and connected to the first end 6 of the pipe 5. The orifice plate 7 is placed within the pipe 5 between the first end 6 and the second end 8 of the pipe 5. The first set of one or more sensors 9 is in communication with the fluid 3 between the first end 6 of the pipe 5 and the orifice plate 7. For example, the first set of one or more sensors 9 may be directly connected with the fluid 3, connected via an electrode, or remotely connected via various methods known in the art such as wirelessly through x-rays, gamma rays, or other methods. The second set of one or more sensors 11 is in communication with the fluid 3 between the orifice plate 7 and the second end 8 of the pipe 5. For example, the second set of one or more sensors 11 may be directly connected with the fluid 3, connected via an electrode, or remotely connected via various methods known in the art such as wirelessly through x-rays, gamma rays, or other methods.

The pump 4 accelerates the fluid 3 into the pipe 5. The first set of one or more sensors 9 measures the amount of air trapped within the fluid 3 before the orifice plate 7. The orifice plate 7 creates a temporary restriction in the pipe 5, creating a low pressure region 13, which expels any dissolved air generating trapped air. The second set of one or more sensors 11 measures the amount of air trapped within the fluid 3 after the orifice plate 7. The generated trapped air is calculated by the difference of the measured amount of trapped air detected by the first set of one or more sensors 9 and the second set of one or more sensors 11. Since the generated trapped air is produced directly from the dissolved air in the fluid 3, the generated trapped air is proportional to the amount of dissolved air in the fluid 3.

The pipe 5 is any device able to contain the fluid 3 during operation of the sensor. Preferably, the pipe 5 is cylindrical and has an aperture central to the pipe 5 and running the length the pipe 5. In the alternative, the pipe 5 may have other shapes, for example rectangular, or triangular. In the preferred embodiment, the pipe 5 is made of a material capable of transporting hydraulic fluid at temperatures between about −40 and 275 degrees Fahrenheit. The preferred diameter of the pipe 5 depends on a variety of factors such as pressure, type of fluid 3, and orifice plate 7. For example, for a hydraulic fluid the pipe 5 preferably has a diameter between about ½ inch to about 2 inches.

The fluid 3 is any substance that is substantially in a liquid state at the temperature and pressure the fluid 3 is exposed to in the pipe 5. In the preferred embodiment, the fluid 3 is hydraulic fluid.

The pump 4 accelerates the fluid 3 into the pipe 5. In the preferred embodiment the fluid 3 is accelerated to between about 1 m/s (meters per second) to about 5 m/s. Examples of suitable pumps are described in U.S. Pat. Nos. 7,168,928; 6,942,468; 6,863,502; 6,764,285 herein fully incorporated by reference.

The orifice plate 7 temporally restricts the flow of the fluid 3 through the pipe 5 whereby the fluid 3 is restricted only for a relatively short period, before normal flow resumes. Preferably, the orifice plate 7 temporally blocks some of the fluid 3 within the pipe 5 from passing through the orifice plate 7. In the preferred embodiment, the orifice plate 7 is a solid structure spanning the entire diameter of the pipe 5 and having a small orifice 10 (aperture) which allows some fluid to pass through the orifice plate 7. Therefore, the orifice plate 7 induces a higher velocity of the fluid in the orifice 10 (to maintain the same mass flow) and consequent reduction in the pressure at the low pressure region 13. Preferably, the orifice plate 7 lowers the pressure at the low pressure region 13 as low as possible without significantly vaporizing the fluid 3. The vaporization of the fluid 3 is preferably minimized as it will be detected as trapped air and incorrectly attributed to dissolved air casing erroneous readings. Preferably, the diameter of orifice 10 is less than half the diameter of the aperture of the pipe 5. More preferably, the diameter of the orifice 10 is about one fourth of the diameter of the aperture of the pipe 5, whereby in an ideal (frictionless) flow would yield near vacuum (less than atmospheric pressure) conditions immediately behind the orifice plate 7. In the preferred embodiment, the orifice 10 is between about $⅛^{th}$ of an inch to about ½ of an inch (but could be larger depending upon the pipe size) and has a length of about $1/16^{th}$ to ¼ of an inch. The orifice 10 can have a variety of shapes, but is preferably a sharp-orifice.

Assuming frictionless flow of an incompressible fluid, the pressure Po at the low pressure region 13 is given by the following equation:

$$Po = P = \frac{1}{2}\rho V^2 \left[ \left(\frac{A}{Ao}\right)^2 - 1 \right]$$

where $\rho$ is the fluid 3 density; A is the cross sectional area of the pipe 5 before the orifice plate 7; V is the velocity of the fluid 3 before the orifice plate 7; P is pressure before the orifice plate 7 (upstream); and Ao is the cross-sectional area of the orifice plate 7.

Therefore, with an appropriate choice of the area ratio (ratio of the cross sectional area of the pipe 5 (A) and the cross sectional area of the orifice 10 (Ao)) and fluid 3 velocity (V), it is possible to get a very low pressure (Po) at the low pressure region 13. The low pressure (Po) at the low pressure region 13 releases dissolved air from the fluid 3 generating trapped air. For example, the following conditions lead to a theoretical Po=0 (vacuum): P=0.11 MPa (15.96 psi); A/Ao=10; V=1.53 m/s; and $\rho$=950 kg/m$^3$.

Other factors may affect the low pressure region 13, such as the shape of the pipe 5 and orifice 10, the pressure of the fluid 3 before it reaches the orifice plate 7, fluid 3 characteristics, and pressure of the fluid 3 after the orifice plate 7 (downstream), and the length (on the axis parallel with the length of the pipe 5) of the orifice 10. In the alternative, multiple orifice plates may be used to create a plurality of low pressure regions.

The first set of one or more sensors 9 and the second set of one or more sensors 11 are each any device capable of determining the amount of trapped air in the fluid 3. The first set of one or more sensors 9 and the second set of one or more sensors 11 may utilize a variety of methods known in the art to determine the amount of trapped air, preferably based on the fluid 3 pressure, pressure drop or dielectric constant. These techniques as known in the art may use various components such as capacitance transducers, pressure transducers, pressure drop sensors, x-ray systems, gamma-ray systems, or combinations thereof.

In one embodiment each set of one or more sensors (first set of one or more sensors 9 and the second set of one or more sensors 11) use one or more capacitance transducers. Examples of capacitance transducer sensors include sensor system similar to the ones described in U.S. Pat. No. 4,282,481, "Design of capacitance sensor system for void fraction measurement," Journal of Zhejiang University Science, ISSN 1009-3095 and Zhiyao H. et. al., and "Application of Electrical Capacitance Tomography to the Void Fraction Measurement of Two-Phase Flow," IEEE Instrumentation and Measurement Technology Conference, Budapest, Hungary, May 21-23, 2001; and LIU Yi-ping et. al. all herein fully incorporated by reference.

As the void fraction in the fluid 3 (the fraction of trapped air in the fluid 3) greatly reduces the effective dielectric constant of the fluid 3 traveling through the pipe 5, the capacitance of electrodes across fluid 3 between two points across the fluid 3 is also reduced. This reduction in the capacitance is directly related to the void fraction which may be used to calculate the trapped air.

Figure 2B:
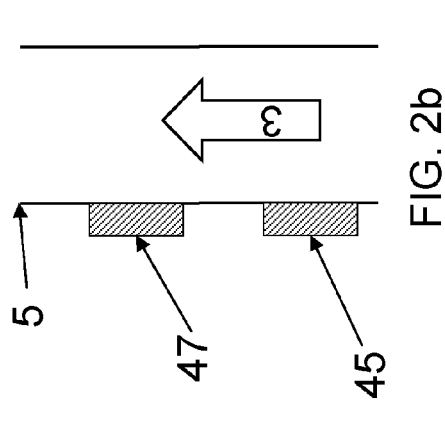
FIG. 2b is an embodiment of one or more sensors using pressure transducers measuring the pressure drop on a vertical pipe.
Figure 2D:
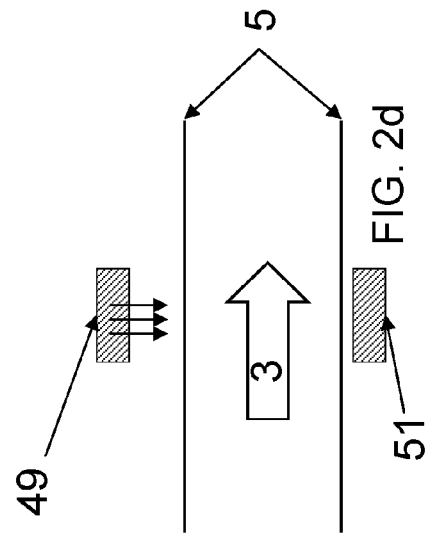
FIG. 2d is an embodiment of one or more sensors using a remote sensing device such as an x-ray, or gamma ray based sensor.
Figure 2A:
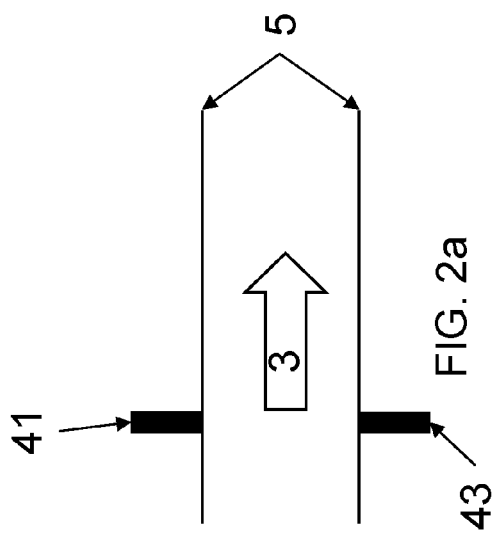
FIG. 2a is an embodiment of one or more sensors using capacitance transducers.

Preferably, each set of one or more sensors 9 contains a first electrode 41 and a second electrode 43 spaced furthest from each other along an axis perpendicular to the length of the pipe 5, as shown in FIG. 2a. As known in the art, other electrode configurations may be used, for example placing the first electrode 41 and the second electrode 43 along the axis parallel the length of the pipe 5. The first electrode 41 and a second electrode 43 can be within the pipe 5 and in contact with the fluid 3, but are preferably outside the pipe 5. If the pipe 5 is electrically conductive, the one or more pairs of electrodes are electrically insulated from the pipe 5, preferably by placing the one or more pairs of electrodes within the pipe 5 wall, but flush with the pipe 5 wall to prevent interference with the fluid 3 flow. Referring back to FIG. 1, the void fraction in the fluid 3 before the orifice plate 7 is then determined from the first set of one or more sensors 9. Likewise, the void fraction in the fluid 3 after the orifice plate 7 is determined from the second set of one or more sensors 11 readings. The difference in the void fraction before the orifice plate 7 (calculated from the first set of one or more sensors 9) and the void fraction after the orifice plate 7 (calculated from the second set of one or more sensors 11) is therefore the fraction of dissolved air in the fluid 3. The fraction of dissolved air in the fluid 3 is used to calculate the amount of dissolved air in the fluid 3. Therefore, the void fraction before the orifice plate 7 subtracted from the void fraction after the orifice plate 7 is the fraction of dissolved air in the fluid 3. In another embodiment, a plurality of pairs of electrodes are equally separated from each other around the pipe 5.

In the preferred embodiment, shown in FIG. 2b, each set of one or more sensors use one or more use pressure transducers to detect pressure drop and determine the void fraction before and after the orifice plate 7. The use of pressure transducers to detect pressure drop and determine void fraction are known in the art, for example the sensor systems described in U.S. Pat. No. 6,557,417; Tutu, N. K., "Pressure Fluctuations and Flow Pattern Recognition in Two-Phase Gas-Liquid Flows", Int. J. Multiphase Flow, (1982), Vol. 8, No. 4, pp. 443-447; and Tutu, N. K., "Pressure Drop Fluctuations and Bubble-Slug Transition in a Vertical Two-Phase Air-Water Flow", Int. J. Multiphase Flow, (1984) Vol. 10, No. 2, pp. 211-216, herein fully incorporated by reference.

In this embodiment the pipe 5 is preferably vertical (length of the pipe 5 running substantially perpendicular to the ground) and the fluid 3 flows in a vertical direction. Each set of one or more sensors comprises a first pressure sensor 45 and a second pressure sensor 47. The first pressure sensor 45 and the second pressure sensor 47 are preferably placed flush against the pipe 5 and in contact with the fluid 3. The first pressure sensor 45 is positioned a predetermined distance away from the second pressure sensor 47. The trapped air measurement is deduced from the well known pressure drop or capacitance probe measurement techniques. For example, for the case in which the pressure drop is dominated by the hydrostatic head (assuming the pipe is oriented in the vertical direction and the frictional pressure drop is relatively very small), the void fraction is directly related to the pressure drop. For this case, the pressure drop per unit length, $\Delta P/\Delta H$ is given by the following equation:

$$\Delta P/\Delta H = [\alpha \rho_v + (1-\alpha)\rho_L]g$$

where $\alpha$ is the void fraction, $\rho v$ is the density of vapor (negligible or close to zero as compared to the density of the liquid in the fluid 3, $\rho L$ is the density of the fluid 3, and g is the acceleration due to gravity. Since $\Delta P/\Delta H$ is measured and the densities and the acceleration due to gravity are known, the void fraction or vapor fraction can be calculated from the above equation. Even when the pressure drop is not dominated by hydrostatic head, it is well known in the art of two-phase fluid dynamics that the mean pressure drop or its statistical fluctuating quantities (probability density function and its moments) can be related to the void fraction when the fluid 3 flow rate is known.

Figure 2C:
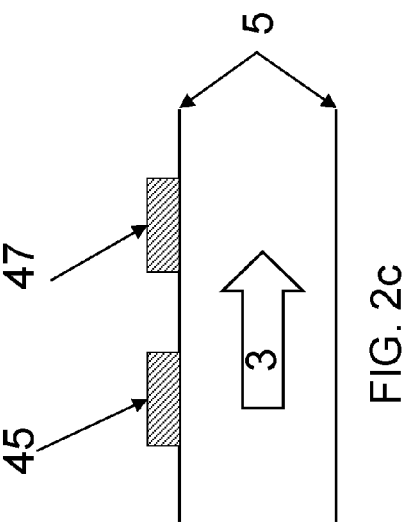
FIG. 2c is an embodiment of one or more sensors using pressure transducers measuring the pressure drop on a horizontal pipe.

In the alternative, the pipe 5 may also be positioned horizontally (substantially parallel to the ground) as described in U.S. Pat. No. 6,557,417. FIG. 2c depicts each set of one or more sensors use one or more use pressure transducers to detect pressure drop and determine the void fraction. Generally, each set of one or more sensors comprises a first pressure sensor 45 and a second pressure sensor 47. The first pressure sensor 45 and the second pressure sensor 47 are preferably placed flush against the pipe 5 and in contact with the fluid 3. The first pressure sensor 45 is positioned a predetermined distance away from the second pressure sensor 47.

Other methods of measuring void fraction of trapped air and combinations thereof can be also used, as known in the art, to determine the amount of increased trapped air, and therefore the amount of dissolved air. For example, one such technique, shown in FIG. 2d, is to use x-ray or gamma-ray source 49 on one end and a corresponding detector 51 on the other side of the pipe 5 to determine the void fraction of the fluid 3 within the pipe 5. Since the absorption coefficient of x-rays or gamma-rays passing through the fluid 3 to the detector is only finite for the liquid phase (and virtually zero for the trapped air), the detector signal is directly proportional to the void fraction of the fluid 3, hence, the void fraction of the fluid 3 can be determined. However, these techniques will generally be more expensive to implement. A thermal neutron source such as the one described in U.S. Pat. No. 3,461,286 hereby fully incorporated by reference, may also be used, but will be extremely expensive and may be difficult to work with smaller pipe 5 diameters.

As dissolved air will not be released from the fluid 3 instantaneously at the orifice plate 7, the second set of one or more sensors 11 is preferably located at a distance away from the orifice plate 7. The time for dissolved gas to be released from the fluid 3 is dependent upon a plurality of factors, such as the fluid 3, the low pressure region 13, temperature, as well as other factors known in the art. The fluid 3 velocity and time for the dissolved gas to be released influence the optimal placement of the second set of one or more sensors 11. Preferably, the location of the second set of one or more sensors 11 is optimally determined for the specific fluid sought to be used. In the preferred embodiment, the first set of one or more sensors 9 is located anywhere from about several inches to within an inch of the orifice plate 7 and the second set of one or more sensors 11 is located anywhere from about one to ten times the diameter of the pipe 5.

Preferably, the first set of one or more sensors 9 and the second set of one or more sensors 11 are each calibrated to the fluid 3, whereby an absolute void fraction may be determined. In the alternative, calibration is foregone, instead relying solely on the difference between the first set of one or more sensors 9 and the second set of one or more sensors 11, whereby only a qualitative indication of dissolved air is determined by the instrument. However, the calibration of such a device is rather simple and easily accomplished.

Figure 3:
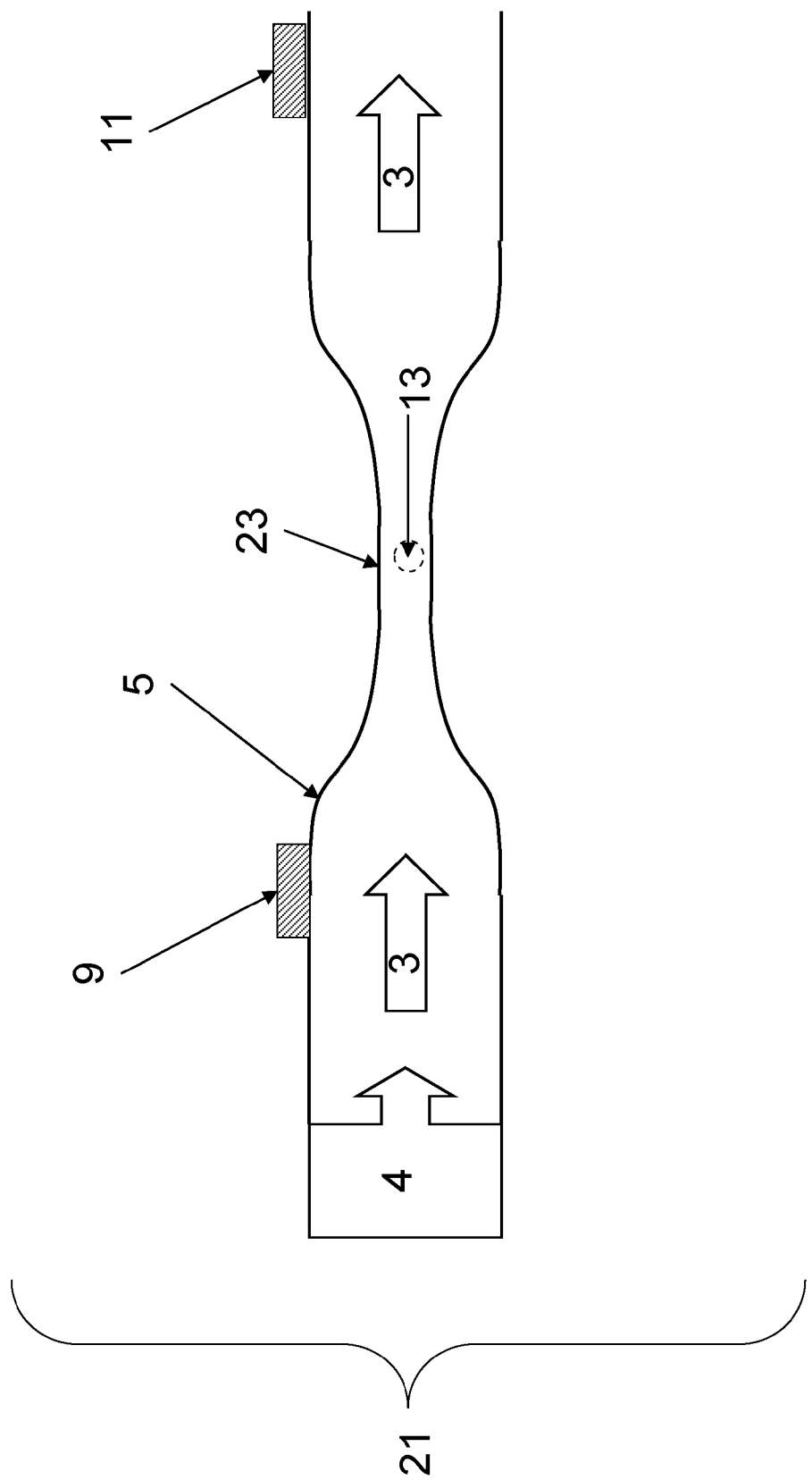
FIG. 3 depicts an embodiment of the present invention utilizing a pipe having a pinched center.

In another embodiment utilizing a pipe having a pinched center 21 shown in FIG. 3, the orifice plate 7 of FIG. 1 is replaced by a pinched pipe section 23. In this embodiment, the first set of one or more sensors 9 determines the amount of trapped air of the fluid 3 before the pinched pipe section 23. Likewise, the second set of one or more sensors 11 determines the amount of trapped air of the fluid 3 after the pinched pipe section 23. Preferably the pipe 5 is a long cylindrical pipe having a pinched center, creating the pinched pipe section 23. In the alternative, a cylindrical pipe having a diameter less than the pipe 5 may be used instead of the pinched pipe section 23. For example the pipe 5 may be two cylindrical tubes separated by a smaller pipe, whereby the pinched pipe section 23 is a smaller pipe. In yet another alternate embodiment, the pipe 5 is a long cylindrical pipe having a raised inner wall section, reducing the effective diameter of the pipe 5. For example, a glass, metal, or ceramic layer may be used in a section of the pipe 5 to reduce the diameter of the pipe 5 creating the equivalent of a pinched pipe section 23. In the alternative, multiple pinched pipe sections may be used to create a plurality of low pressure regions.

Figure 4:
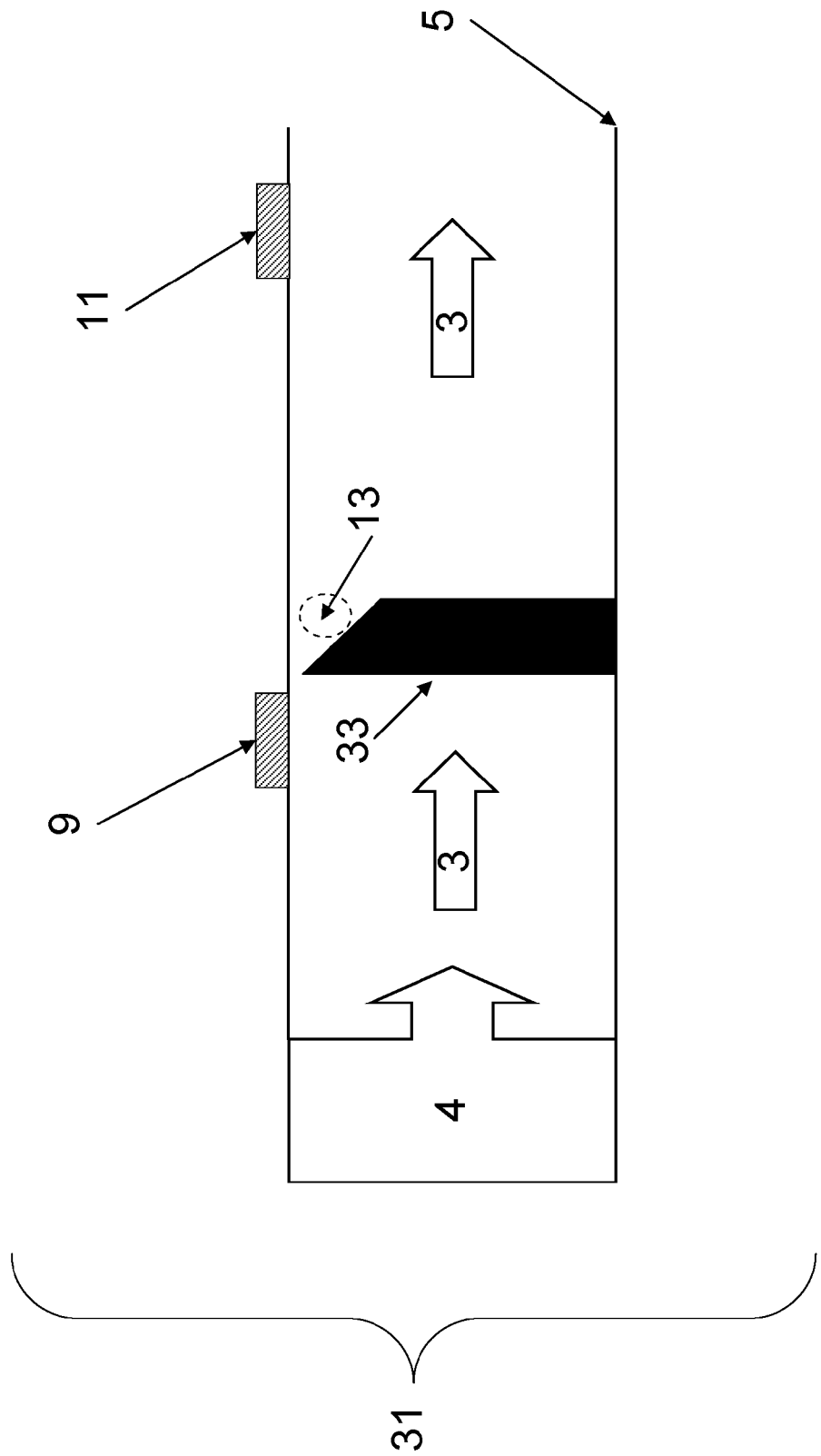
FIG. 4 depicts an embodiment of the present invention utilizing a pipe having a straight wall, partially blocking the flow of a fluid.

In yet another embodiment utilizing a pipe having a straight wall 31 shown in FIG. 4, the orifice plate 7 of FIG. 1 is replaced by a straight wall 33. Preferably the pipe 5 is a long cylindrical pipe having a straight wall 33, which restricts the flow of the fluid 3 through the pipe 5. The straight wall 33 restricts the fluid 3 as it flows through the pipe 5. Preferably, the straight wall 33 runs substantially perpendicular to the length of the pipe 5. More preferably, the straight wall 33 runs perpendicular to the length of the pipe 5. In this embodiment, the straight wall 33 is connected to the inner wall of the pipe 5 and extends through the middle of the pipe 5 and towards the top edge of the pipe 5. The width and height of the straight wall 33 may be optimized for factors such as the pipe 5, fluid 3, fluid 3 velocity, etc. . . . More preferably, the straight wall 33 is connected to the inner wall of the pipe 5, and extends a sharp edge through the middle of the pipe 5 and towards the top edge of the pipe 5. In an alternate embodiment, the straight wall 33 covers the middle of the pipe 5. The straight wall 33 may be made of various materials, for example, the material of the pipe 5, glass, metal, or ceramic. The straight wall 33 may have a variety of shapes, for example circular, triangular, rectangular, or a combination thereof. In the preferred embodiment, the straight wall 33 has an circular shape, restricting all fluid 3 except for a small portion at the edge of the straight wall 33. In this embodiment, the first set of one or more sensors 9 determines the amount of trapped air of the fluid 3 before the straight wall 33. Likewise, the second set of one or more sensors 11 determines the amount of trapped air of the fluid 3 after the straight wall 33. In the alternative, multiple straight walls may be used to create a plurality of low pressure regions.

As some dissolved air may not be released by the low pressure region 13, it may be desirable to either calibrate the sensor to deal with the dissolved air that is not released, or pass the fluid 3 through the low pressure region 13 multiple times to insure all dissolved gas is accounted for. For example, the fluid 3 may go through the same dissolved gas sensor in multiple passes, or go through any number of dissolved gas sensors connected in series. In yet another alternate embodiment, multiple sensors may be connected in parallel to measure a larger sample of fluid 3, for increased resolution, or to better account for heterogeneous fluids. In still yet another embodiment, the fluid 3 is passed through multiple orifice plates, pinched pipes section, a straight walls or combinations thereof in parallel.

It is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements.

All publications and patent documents cited in this application are incorporated by reference in their entirety for all purposes to the same extent as if each individual publication or patent document were so individually denoted.

Any element in a claim that does not explicitly state "means for" performing a specified function, or "step for" performing a specific function, is not to be interpreted as a "means" or "step" clause as specified in 35 U.S.C. §112, ¶6. In particular, the use of "step of" in the claims herein is not intended to invoke the provisions of 35 U.S.C. §112, ¶6.

The embodiment of the invention in which an exclusive property or privilege is claimed is defined as follows:

1. A method for the detection of dissolved gas in a fluid, substantially in liquid state, comprising the steps of:
    a. Pumping a fluid into a pipe;
    b. A restricting step for temporarily restricting the flow of said fluid through said pipe creating one or more low pressure regions whereby said low pressure regions have a pressure of about a perfect vacuum;
    c. Measuring parameters of said fluid and calculating the amount of trapped air within said fluid before said restriction step, within said pipe, using said parameters, creating a first measurement;
    d. Measuring parameters of said fluid and calculating the amount of trapped air within said fluid after said restriction step, within said pipe, using said parameters, creating a second measurement; and
    e. Calculating the amount of dissolved gas in said fluid from said first and said second measurement.

2. The method for the detection of dissolved gas in a fluid of claim 1 whereby said restricting step creates one or more low pressure regions having a pressure greater than the pressure required to substantially vaporize said fluid.

3. The method for the detection of dissolved gas in a fluid of claim 1 whereby said step of measuring the amount of trapped air employs the use of one or more capacitance transducers.

4. The method for the detection of dissolved gas in a fluid of claim 1 whereby said step of measuring the amount of trapped air employs the use of one or more pressure transducers.

5. The method for the detection of dissolved gas in a fluid of claim 1 whereby said steps are performed at least once a second.

6. The method for the detection of dissolved gas in a fluid of claim 1 whereby:

a. Said pipe has a length and an aperture running along said length of said pipe having a first end and a second end;
b. An orifice plate positioned within said aperture between said first end and said second end; and
c. Said orifice plate positioned perpendicular to said length of said pipe, whereby said fluid is restricted by, but allowed to pass through said orifice plate.

7. The method for the detection of dissolved gas in a fluid of claim 6 whereby said orifice plate comprises a sharp-edged orifice.

8. The method for the detection of dissolved gas in a fluid of claim 6 whereby:
   a. Said pipe has a diameter;
   b. Said orifice plate comprises an orifice having a diameter; and
   c. Said diameter of said pipe has at least about twice the area of said diameter of said orifice.

9. The method for the detection of dissolved gas in a fluid of claim 6 whereby:
   a. Said pipe has a diameter;
   b. Said orifice plate comprises an orifice having a diameter; and
   c. Said diameter of said pipe has about ten times the area of said diameter of said orifice.

10. The method for the detection of dissolved gas in a fluid of claim 1 whereby:
    a. said first measurement step comprises a means for measuring pressure drop; and
    b. said second measurement step comprises a means for measuring pressure drop.

11. The method for the detection of dissolved gas in a fluid of claim 10 whereby:
    a. said first measurement means comprises one or more pressure transducers; and
    b. said second measurement means comprises one or more pressure transducers.

\* \* \* \* \*